United States Patent [19]
Landry et al.

[11] Patent Number: 5,063,780
[45] Date of Patent: Nov. 12, 1991

[54] ULTRASONIC DIMENSIONAL AND FLAW INSPECTION OF THIN-WALLED TUBULAR ELEMENTS

[75] Inventors: James D. Landry; Frederick C. Schoenig, Jr., both of Wilmington, N.C.; John D. Young, Rexford, N.Y.

[73] Assignee: General Electric Company, San Jose, Calif.

[21] Appl. No.: 480,465

[22] Filed: Feb. 15, 1990

[51] Int. Cl.$^5$ .................................................. G01N 29/06
[52] U.S. Cl. .................................. 73/622; 73/624; 73/625; 364/507
[58] Field of Search ................ 73/597, 622, 624, 625, 73/638, 637; 364/507

[56] References Cited
U.S. PATENT DOCUMENTS

| 3,828,609 | 8/1974 | Furon et al. | 73/622 |
| 3,930,404 | 1/1976 | Ryden, Jr. | 73/622 |
| 4,373,395 | 2/1983 | Borburgh et al. | 73/607 |
| 4,456,982 | 6/1984 | Tournois | 73/624 |
| 4,653,505 | 3/1987 | Iinuma | 73/597 |
| 4,699,007 | 10/1987 | Kawashima et al. | 73/622 |
| 4,716,765 | 1/1988 | Hirama | 73/626 |
| 4,766,554 | 8/1988 | Sarr et al. | 364/507 |

Primary Examiner—Hezron E. Williams
Assistant Examiner—Rose M. Finley
Attorney, Agent, or Firm—R. R. Schroeder

[57] ABSTRACT

A quality assurance inspection system utilizes a plurality of ultrasonic transducers to probe an elongated tube for both dimensional and structural integrity. The transducers are pulsed in rapid succession, and echo signals are conducted over separate RF channels and through a multiplexor to a lesser number of detector signals channels, each including a discriminator. Inspection windows are opened in these discriminators to permit detection of echo signals and the generation of time mark signals for stopping a plurality of clocks which then register pulse-echo time intervals. These data are computer processed to provide tube dimension and flaw information.

10 Claims, 4 Drawing Sheets

ULTRASONIC DIMENSIONAL AND FLAW INSPECTION OF THIN-WALLED TUBULAR ELEMENTS

The present invention relates to apparatus for performing quality assurance examinations of thin walled tubular elements.

BACKGROUND OF THE INVENTION

In certain applications, the dimensional and structural integrity of certain critical components is of the utmost importance to assure against future service failures. An example of one such critical component is the cladding tube of a nuclear fuel rod, which contains the fuel pellet column. Plugs are welded to the open ends of the cladding tube to seal the pellet column therein. Cladding tubes must be manufactured to exacting standards of structural integrity if they are to withstand the high internal pressures developed over the long service life of nuclear fuel rods. That is, flaws, such as cracks, pores, etc., in the tube wall cross section, depending on their size, number and location, can render a cladding tube unsafe for use in a nuclear fuel rod.

Cladding tubes must also meet exacting dimensional standards. The inner diameter must be precisely controlled such that fuel pellets can be properly loaded therein. The same is true of the outer diameter so that the fuel rods can be properly assembled into fuel bundles. Wall thickness is also a rejection criteria, as a thin wall section less than a minimum tolerance dimension jeopardizes internal pressure withstandability.

In view of the critical nature of nuclear fuel rod cladding tubes, it is necessary to non-destructively inspect each and every cladding thoroughly over its entire length for both dimensional and structural integrity before it is accepted for use in a nuclear fuel rod. Ultrasonic inspection using a transducer operated in a pulse-echo mode is now being commonly utilized to examine critical components for quality assurance. The transducer is scanned over the component, by motion of the transducer and/or the component, while the transducer is periodically electrically excited to emit a probing ultrasonic energy pulse and, in the intervals between pulses, receives the echoes containing inspection information. The time required to fully inspect each component is largely dependent on scanning speed. Obviously, the scanning speed can not be so great that the transducer "runs away" from the probing energy pulse, such that it does not adequately receive the echoes associated with each pulse. To offset this limitation on scanning speed, multiple transducers have been utilized to reduce inspection time. This approach adds tremendously to the hardware cost of an ultrasonic inspection system, since each transducer calls for a separate signal channel, each with its own set of electronics for extracting inspection information from the echo signals.

It is accordingly an object of the present invention to provide an improved system for ultrasonically inspecting manufactured components.

A further object is to provide an ultrasonic inspection system of the above-character, which is capable of performing complete quality assurance inspection of manufactured components on an expedited, automated basis.

An additional object is to provide an ultrasonic inspection system of the above-character for quality assurance inspection of elongated, thin-walled tubular elements.

Another object is to provide an ultrasonic inspection system of the above-character for inspecting tubular elements for adherence to dimensional manufacturing standards and for the presence of structural flaws.

A still further object is to provide an ultrasonic inspection system of the above-character, which is economical in cost and efficient in operation.

Other objects of the invention will in part be obvious and in part appear hereinafter.

SUMMARY OF THE INVENTION

In accordance with the present invention, there is provided a system for conducting complete dimensional and flaw ultrasonic inspection of elongated, thin-walled tubular elements, such as cladding tubes for nuclear fuel rods. To reduce the time required to fully inspect each tube, the system utilizes multiple transducers which are operated in a manner to make efficient use of the pulse-echo time intervals for each transducer without significant increase in electronic hardware costs. To this end, the system includes a pair of ultrasonic transducers for dimensionally inspecting a tube along respective helical scanning paths to obtain measurements of outer diameter, inner diameter and wall thickness at closely spaced dimensional inspection points throughout the entire tube length. The system further includes an additional plurality of transducers for inspecting the tube for flaws at closely spaced flaw inspection points along respective spiral paths throughout the entire tube length. A separate driver electrically excites each transducer to emit its probing ultrasonic energy pulse, and the echoes received by each transducer are conducted as echo signals over separate RF signal channels to different inputs of a multiplexor.

The echo signals on the single output of the multiplexor are amplified and then split for conduction over a plurality of detector signal channels, each including a discriminator. A separate gate generator opens an inspection window in each discriminator during which a discriminator can, in response to the detection of an echo signal appearing in its signal channel, generate a time mark signal. These time mark signals are separately applied to stop a plurality of clocks, which then register the pulse-echo time intervals for each transducer. These time interval data are processed by a computer to obtain the tube dimensions at each dimensional inspection point and to indicate the existence of a flaw at any of the flaw inspection points.

To coordinate system operation in time efficient fashion, a synchronizer issues a repeating succession of timing pulses for 1) triggering the drivers in sequence to cause the transducers to emit probing ultrasonic energy pulses, 2) indexing the multiplexor to route successive echo signals from the transducers through to the detector signal channels, and 3) triggering the generation of the discriminator inspection windows, such that the time intervals registered by the various clocks are properly correlated with the proper dimensional and flaw inspection transducers.

The invention accordingly comprises the features of construction, combination of elements, and arrangement of parts, all as described below, and the scope of the invention will be indicated in the claims.

BRIEF DESCRIPTION OF THE DRAWINGS

For a full understanding of the nature and objects of the invention, reference may be had to the following Detailed Description taken in connection with the accompanying drawings, in which.

Corresponding reference numerals refer to like parts throughout the several views of the drawings.

DETAILED DESCRIPTION

Figure 1:
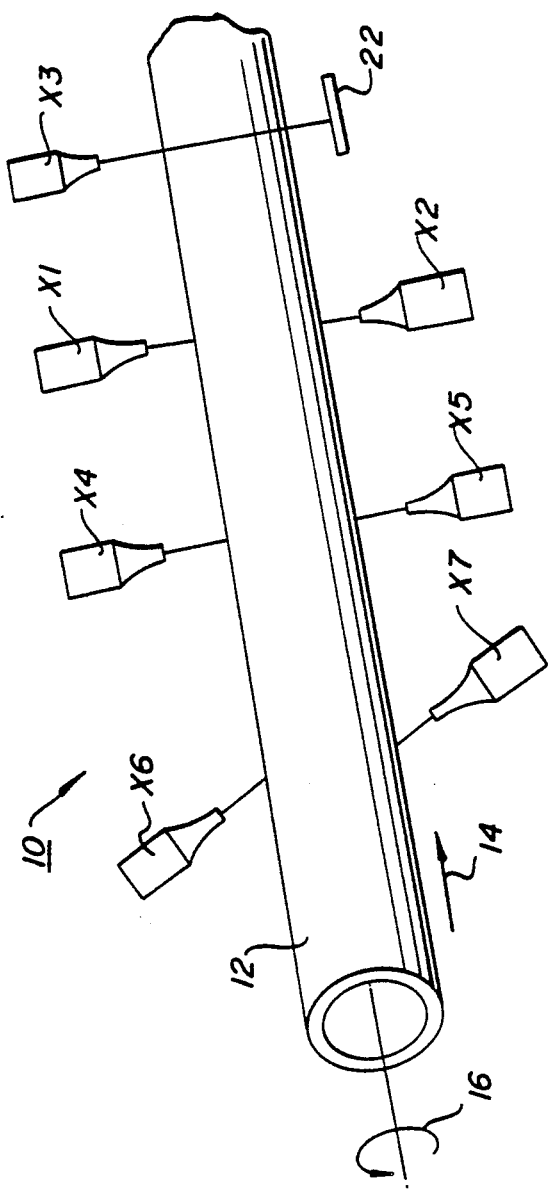
FIG. 1 is a diagrammatic perspective view of an ultrasonic inspection station utilized in the system of the present invention for inspecting thin-walled tubular elements.

The ultrasonic inspection system of the present invention, as seen in FIG. 1, utilizes at least seven ultrasonic transducers X1 through X7 mounted by suitable means (not shown) at an inspection station, generally indicated at 10, through which a metal tube 12 to be inspected passes axially or longitudinally, as indicated by arrow 14, while being rotated about its axis, as indicated by arrow 16. It will be appreciated that the tube and transducers are immersed in a bath (not shown) of a suitable liquid couplant, such as water, serving to provide effective coupling into the tube wall of the highly focused beams of probing ultrasonic energy pulses emitted by the transducers. Since the tube is moving both axially and rotationally, these probing beams trace individual, tightly pitched helical scanning paths over the tube peripheral surface throughout its length. The transducer pulsing rate is sufficiently rapid to ensure thorough inspection of the entire tube cross section for both dimensional acceptance and the presence of flaws. It will be appreciated that, rather than rotating the tube, helical scanning may be achieved by revolving the transducers about the tube axis as the tube is conveyed axially through the inspection station.

Figure 2:
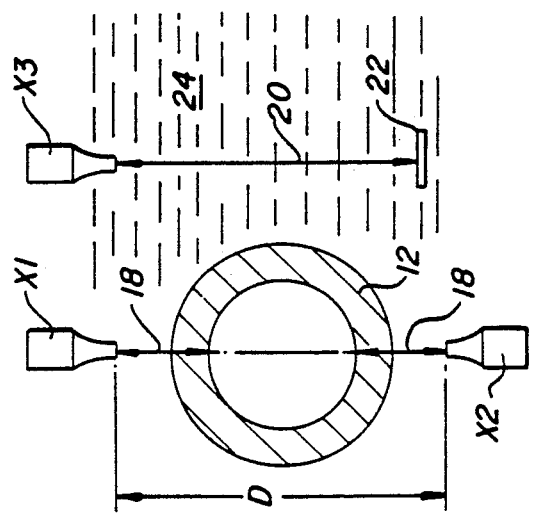
FIG. 2 is a diagrammatic sectional view illustrating the dimensional inspection ultrasonic transducers and the fluid couplant temperature compensating transducer utilized in the inspection station of FIG. 1.

Of the ultrasonic transducers seen in FIG. 1, transducers X1 and X2 are utilized for dimensional inspection of the tube, which may be a nuclear fuel rod cladding tube. Thus, as seen in FIG. 2, these two transducers are positioned on opposite sides of tube 12 with their ultrasonic energy beams 18 in diametrically aligned relation. The transducers are separated by a known, fixed distance D. When transducers X1 and X2 are electrically pulsed to emit ultrasonic energy pulses, commonly referred to in the art as "main bang" pulses, a succession of echoes of each main bang pulse are received back from the outer tube surface, the inner tube surface, and a second echo from the inner tube surface. As will be seen, these three echoes received by each transducer X1 and X2 are processed together with dimension D to determine the outer diameter, inner diameter, and wall thickness at a multiplicity of closely spaced inspection points distributed circumferential and axially along the entire tube length.

FIG. 2 also shows transducer X3 utilized to enable compensation of the echo receipt times relative to the main bang pulses for all of the inspection transducers for variations in liquid couplant temperature. As is well recognized in the art, the propagation velocity of ultrasonic energy through the couplant does vary with the temperature thereof. For example, the speed of sound in water varies 0.3% for each degree centigrade change in temperature. Thus, to achieve precise measurements of dimensionally small tube wall thicknesses, couplant temperature variations must be taken into account. Transducer X3 is therefore positioned to direct a beam 20 of periodic ultrasonic energy pulses at a target 22, and the pulse-echo propagation times through the couplant 24 are processed to derive temperature-dependent correction factors for use in processing the through-couplant pulse-echo elapsed times for the inspection transducers.

Figure 3:
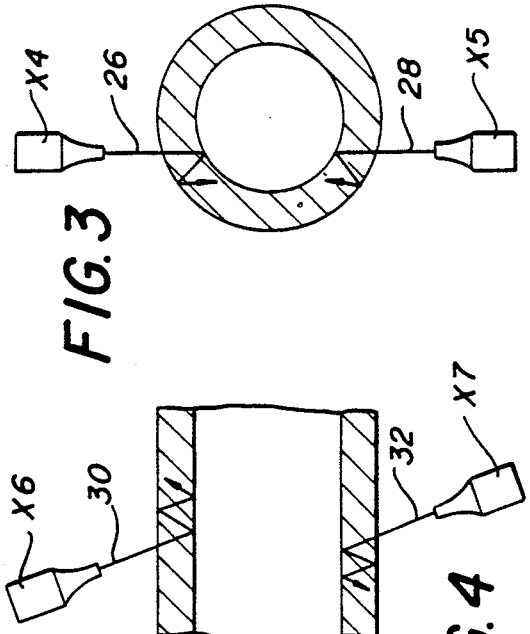
FIG. 3 and 4 are diagrammatic sectional views illustrating the flaw inspection ultrasonic transducers utilized in the inspection station of FIG. 1.

As seen in FIG. 3, transducers X4 and X5 are positioned relative to tube 12 so as to probe the tube wall circumferentially for flaws, such as voids, cracks, etc. Thus, transducer X4 is oriented to direct its highly focused beam 26 to impinge on tube outer surface inspection sites at a suitable oblique angle relative to tangent, such that the ultrasonic energy pulses are reflected between the inner and outer tube surfaces in zig-zag paths. As seen in FIG. 3, the ultrasonic energy pulses emitted by transducer X4 follow zig-zag paths circumferentially through the tube wall in the counter clockwise direction. On the other hand, transducer X5 directs its beam 28 against the tube outer surface at the same oblique angle, such that the ultrasonic energy pulses coupled into the tube wall are reflected between the tube inner and outer surfaces along zig-zag paths extending circumferentially in the clockwise direction.

In the absence of flaws, virtually no ultrasonic energy propagates back to the transducers as echoes. If flaws are present, the amplitudes of the echoes are highly dependent on flaw orientation. If the major dimension of a flaw lies in a plane parallel to the zig-zag paths, the echo amplitude may be too low to detect. However, if the flaw major dimension lies in a plane substantially normal to the zig-zag paths, sufficient ultrasonic energy is reflected back by the flaw to produce a detectable echo.

Figure 4:
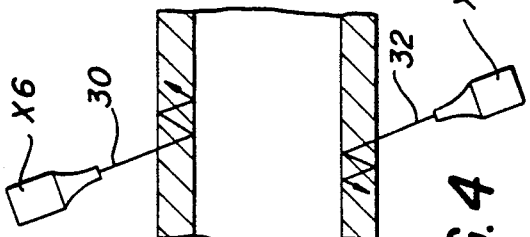

Inspection transducers X6 and X7 are oriented to project their beams 30 and 32 at oblique angles to the tube periphery so as to probe the tube wall in opposing longitudinal directions. Thus, as seen in FIG. 4, ultrasonic energy pulses from transducer X6 are coupled into the tube wall and reflect between inner and outer tube surfaces in zig-zag paths extending longitudinally to the right. Energy pulses from transducer X7 probe the wall cross section along zig-zag paths extending longitudinally to the left. Again, no echoes are received in the absence of flaws. Flaws lying predominately in planes substantially parallel to these longitudinally directed zig-zag paths reflect echoes of minimal amplitudes, while flaws lying in planes substantially normal thereto reflect echoes of meaningful amplitudes. It is thus seen that, from the multi-directional probings of transducers X4 through X7, all flaws of rejectable size included in the tube wall will be detected by at least one of these transducers regardless of flaw orientation. The echo amplitudes from a particular flaw are processed to provide an indication of its size and character, and the pulse-echo elapsed times are processed to indicate its location, e.g., whether it is in or near the inner or outer tube surfaces. Flaw size and location in the tube wall are the major factors involved in the tube accept-reject criteria.

Figure 5:
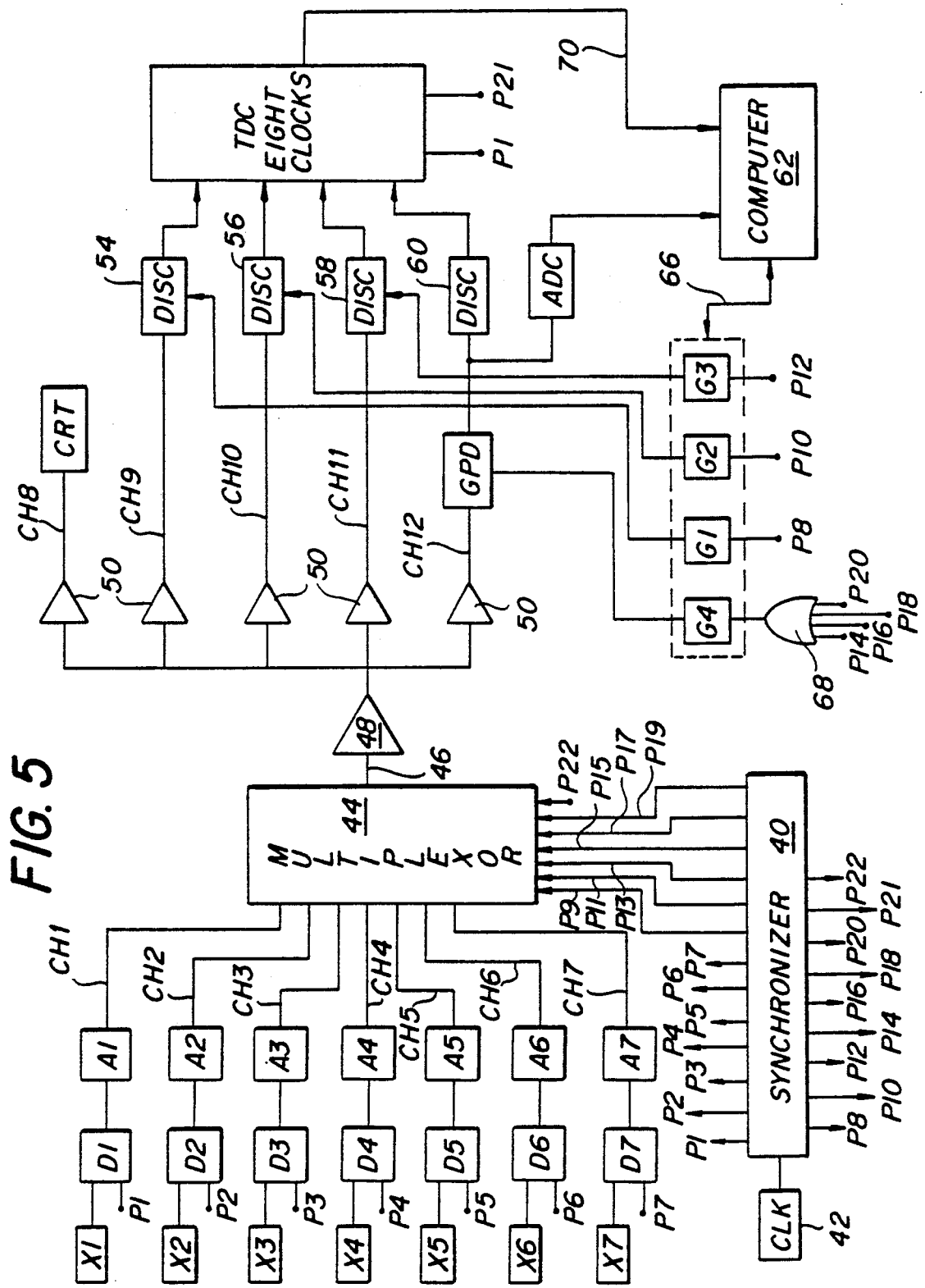
FIG. 5 is a circuit block diagram of the ultrasonic inspection system of the present invention.

To collect the echo inspection information obtained by transducers X1 and X7 in an expeditious, cost effective manner pursuant to the present invention, the signal processing network of FIG. 5 is utilized. As seen therein, transducers X1 through X7 are individually electrically excited to emit their main ultrasonic energy pulses by pulsers or drivers D1 through D7, respectively. These drivers are triggered to electrically pulse their respective transducers by pulses P1 through P7 issued in rapid succession by a synchronizer 40, whose operation is timed by a clock 42. The echo responses of these transducers are routed over separate RF channels CH1 through CH7 including separate attenuators A1 through A7, respectively, to separate inputs of a multiplexor 44. These attenuators are separately, programmably adjusted to account for the varying sensitivities of the transducers. The multiplexor is indexed by synchronizer pulses P9, P11, P13, P15, P17 and P19 to successively connect each of the RF channels through to its single output line 46 in synchronism with the appearance of RF echo signals therein.

The multiplexor output signal is amplified by an amplifier 48 and equally split into five channels CH8 through CH12, each including an amplifier 50. Channel CH8 feeds the echo signals to a cathode ray tube oscilloscope CRT for visual observation. The echo signals on channel CH9 through CH11 are applied to a time-to-digital converter TDC through separate discriminators 54, 56 and 58. The echo signals in channel CH12 are detected by a gated peak detector GPD and discriminated by a separate discriminator 60 before being applied to converter TDC. The output of the gated peak detector is also fed through an analog-to-digital converter ADC to a computer 62 for analysis as to flaw size. In practice, converter ADC may be incorporated in detector GPD. Converter TDC is equipped with eight separate clocks capable of being commonly started and independently stopped in response to time mark signals received from the discriminators. The times registered by each of these eight clocks are digitally encoded and fed to computer 62 at the end of each inspection cycle. A converter known to possess these operating characteristics is a LeCroy Model 4208 time-to-digital converter.

Discriminators 54, 56, 58 and 60 are preferably of the constant fraction type, such as EG&G ORTEC Model 584 discriminators. With such discriminators, a time mark signal output is generated to indicate when the wavefront of any echo signal achieves a level that is always a constant fraction of its ultimate peak amplitude. As a result, the timing of the discriminator time mark signals is relatively immune to echo signal amplitude above a predetermined threshold.

To create inspection windows precisely defined in time during which the echo signals on channels CH9 through CH12 are observed, discriminators 54, 56 and 58 and gated peak detector GPD are selectively gated by a series of four gate generators G1 through G4. Thus, generator G1 generates a gate pulse to open an inspection window in discriminator 54. The gate pulses issued by generator G2 open inspection windows in discriminator 56, while generator G3 serves the same purpose with respect to discriminator 58. The gate pulses of generator G4 open inspection windows in detector GPD. The widths of these gate pulses issued by generators G1–G4 and thus the durations of the inspection windows are independently programmable by computer 62, as indicated by link 66. The timings of these gate pulses are controlled by pulses generated by synchronizer 40. Thus, as seen in FIG. 5, synchronizer pulses P8, P10 and P12 trigger generators G1–G3, respectively, to generate their gate pulses, while synchronizer pulses P14, P16, P18 and P20 are ORed together in a gate 68 to trigger the issuance of four successive gate pulses by generator G4. In practice gate generator G4 may take the form of four separate gate generators respectively triggered by synchronizer pulses P14, P16, P18 and P20 with the generator output pulses ORed together to gate peak detector GPD. This enables the computer to individually program the widths of the gate pulses and thus the widths of the inspection windows opened in the gated peak detector.

Figure 6:
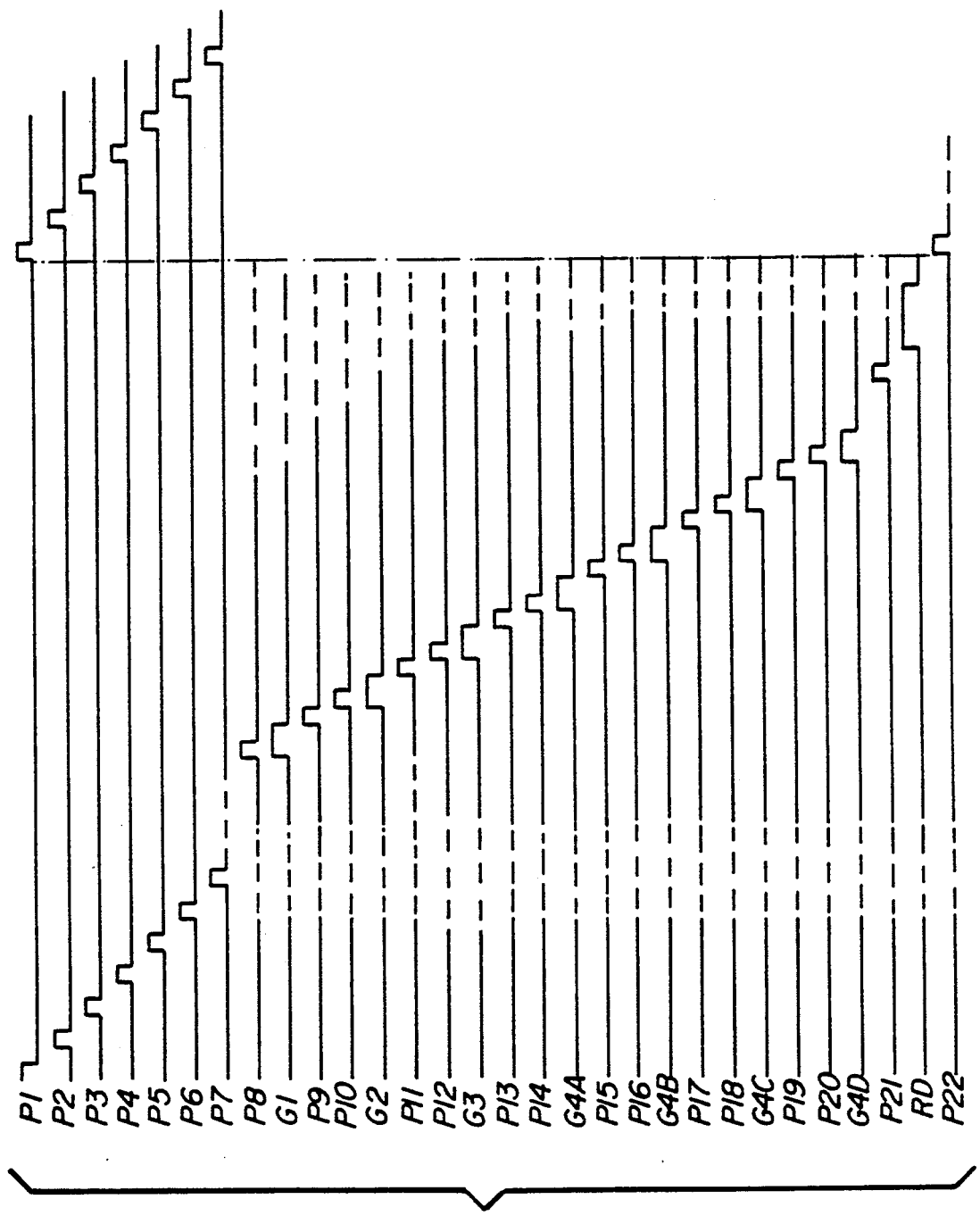
FIG. 6 is a timing signal diagram illustrating the operation of the system of FIG. 5.

To explain the operation of the echo signal processing network of FIG. 5, reference is also made to FIG. 6 illustrating the relative timings of synchronizer pulses P1 to P22. Each inspection cycle is initiated with the issuance of synchronizer pulse P1 triggering driver D1 to pulse transducer X1 into generating its main bang ultrasonic energy pulse. Pulse P1 is also applied to common start the eight clocks in converter TDC. Synchronizer pulses P2 through P7 follow in rapid succession as seen in FIG. 6 to initiate the main bang pulses of transducers X2 through X7. Multiplexor 44 is initialized at the beginning of each inspection cycle with channel CH1 connected through to its output line 46. After an appropriated delay timed to the return of measurement probing echoes to transducer X1, synchronizer pulse P8 triggers generator G1 to open the discriminator 54 inspection window. This condition is illustrated in FIG. 6 by timing line G1. Upon termination of gate pulse G1 to close this inspection window, synchronizer pulse P9 indexes multiplexor 44 to channel CH2, and then synchronizer pulse P10 issues to trigger generator G2 into issuing its gate pulse to open an inspection window in discriminator 56. Upon closure of this window, synchronizer pulses P11 switches the multiplexor to channel CH3, and synchronizer pulse P12 triggers generator G3 to open an inspection window in discriminator 58. Synchronizer pulses P13–P20 follow in succession to step the multiplexor through channels CH4–CH7 and to trigger generator G4 to open four successive inspection windows in gated peak detector GPD, all as seen in FIG. 6.

Synchronizer pulse P21 then issues to signal the end of an inspection cycle and is used to reset to zero those clocks in converter TDC that were not stopped by output signals from discriminators 54, 56, 58 and 60. This pulse P21 is also used by the converter to signal computer 62 to accept digital data over cable 70 indicating the elapsed times registered by each of the eight clocks. This data readout occurs during the interval RD seen in FIG. 6. Finally, synchronizer pulse P22 issues to initialize multiplexor 44 to channel CH1 and to initiate another inspection cycle marked by the issuance of pulse P1. Inspection cycles are automatically repeated to thoroughly inspect a tube throughout its entire length both dimensionally and for flaws.

Figure 7:
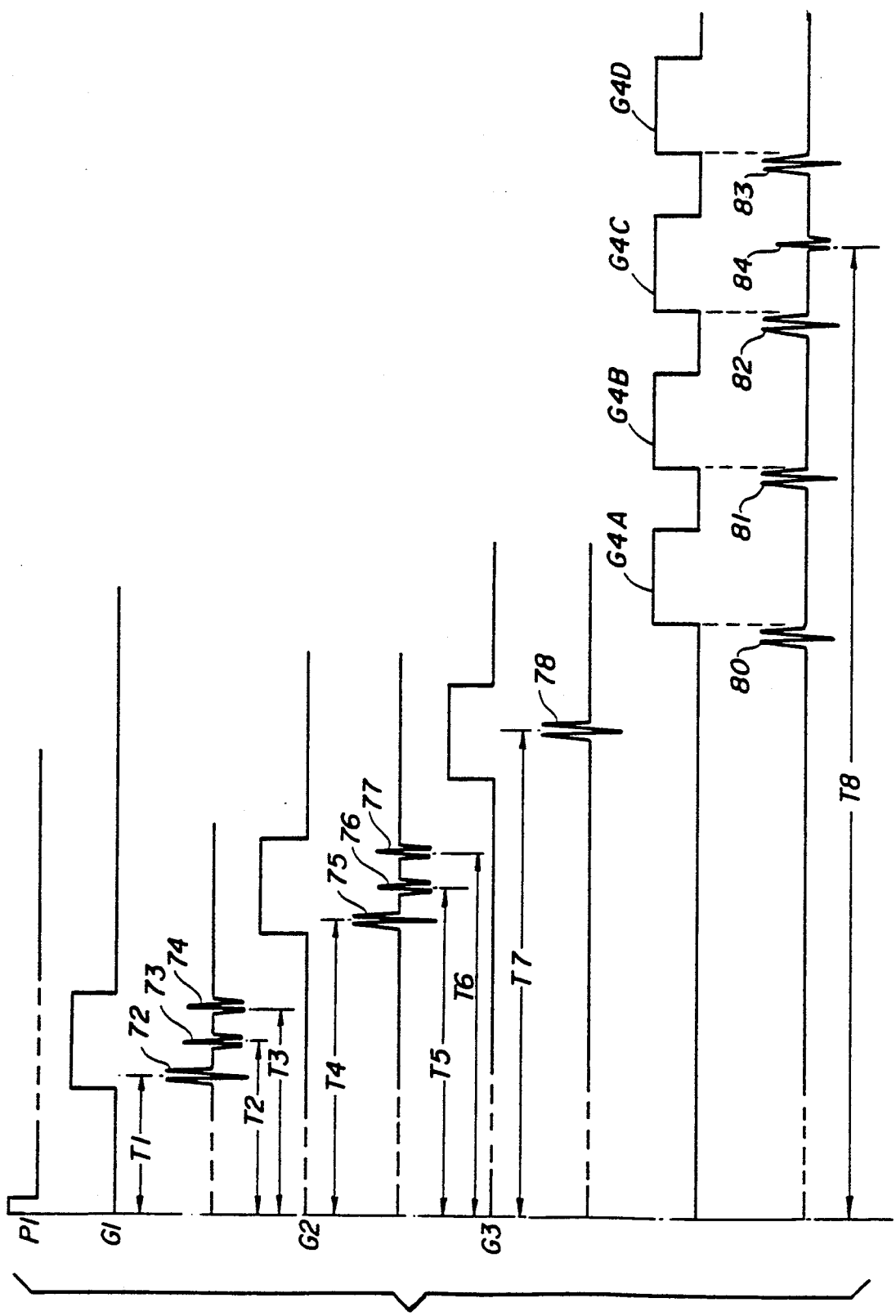
FIG. 7 comprises signal diagrams illustrating of the operation of the echo signal discriminators in FIG. 5.

The operation of converter TDC can best be understood by reference to FIG. 7. As previously noted, synchronizer pulse P1 begins each inspection cycle by triggering driver D1 to initiate the main bang pulse of transducer X1. Time line G1 in FIG. 7 illustrates the inspection window opened in discriminator 54 to detect the echoes received by this transducer in response to its main bang ultrasonic energy pulse. With joint reference to FIGS. 2 and 7, the first signal 72 appearing in this inspection window is the echo reflected back to transducer X1 from the outer surface of tube 12, while signal 73 is the echo reflected from the boundary of the inner tube surface with its open bore which is filled with air or couplant fluid. The third signal 74 occurring in the G1 inspection window is the echo of ultrasonic energy ricocheting from the boundary of the outer tube surface and couplant 24 to the inner tube surface boundary and then back to transducer X1. In response to echo signal 72, discriminator 54 outputs a first time mark signal to converter TDC (FIG. 5) stopping one of its eight clocks at elapsed time T1 measured from synchronizer pulse P1. Discriminator 54 outputs a second time mark signal in response to echo signal 73 to stop a second detector clock at elapsed time T2 and a third time mark signal to stop a third detector clock at elapsed time T3, all as illustrated in FIG. 7.

The G2 inspection window is then opened in discriminator 56 to detect the outer tube surface echo signal 75, the inner tube surface echo signal 76, and the ricocheted echo signal 77 received by transducer X2. The discriminator time mark signals issued in response to echo signals 75-77 stop the next three converter clocks at elapsed times T4, T5 and T6, respectively.

From these six clock counts, computer 62 has sufficient data to calculate the tube dimensions at the particular diametrically opposed inspection points probed by transducers X1 and X2 during each inspection cycle. That is, substrating the distances calculated from elapsed times T1 and T4 from distance D separating transducers X1 and X2 gives the tube outer diameter. Tube wall thickness at the transducer X1 inspection site is calculated from the difference between elapsed times T2 and T3. Similarly, wall thickness at the transducer X2 inspection site is calculated by the computer from the difference between elapsed time counts T5 and T6. The tube inner diameter can then be calculated from the determined outer diameter and two wall thickness determinations.

As noted above, to achieve precise tube dimensional measurements, it is necessary to compensate for couplant temperature variations. Thus the G3 inspection window in discriminator 58 is opened to detect the echo signal 78 reflected from target 22 back to transducer X3 (FIG. 2). In response to this signal, discriminator 58 outputs a time mark signal stopping the seventh clock in converter TDC at elapsed time T7 from synchronizer pulse P1, as seen in FIG. 7. Computer 62 uses this elasped time count T7 to correct the elapsed time counts T1-T6 and thus the tube dimension calculations for changes in sound propagation velocity in the fluid couplant 24 due to variations in its temperature.

Still referring to FIG. 7, the four successive inspection windows opened in gated peak detector GPD in response to synchronizer pulses P14, P16, P18 and P20 are indicated at G4A, G4B, G4C and G4D. These windows are timed to open immediately after receipt of echo signals 80-83 by transducer X4-X7, respectively, from the outer tube surface (FIGS. 3 and 4). In the absence of flaws, no echoes are received in these inspection windows, as indicated in the case of windows G4A, G4B and G4D. However, if a flaw is encountered by the ultrasonic energy propagating in its zig-zag path through the tube wall, a flaw echo will be received in one of these inspection windows, such as flaw signal 84 received by transducer X6 and located within window G4C. The peak to peak value of this flaw signal is digitized in analog-to-digital converter ADC and entered in computer 62 as an indication of flaw size. Also, in response to this flaw signal 84, discriminator 60 outputs a time mark signal to stop the eighth clock in converter TDC at elapsed time T8. This time count is processed by the computer to determine which flaw inspection transducer X4-X7 received the flaw echo and the flaw location within the tube wall cross section. If no flaw signal is detected during an inspection cycle, the eighth converter clock is zeroed by synchronizer pulse P21, and the resulting zero count is interpreted by the computer as an absence of a flaw.

It will be appreciated that converter TDC could be readily equipped with additional clocks to handle the extremely remote possibility of flaw signals being detected in several or even all four inspection windows G4A-G4D during a single inspection cycle. Alternatively, the four flaw inspection transducer echo signals could be handled over separate signal channels rather than the single channel CH12, with each flaw signal channel being connected to a separate clock in converter TDC.

It will be further appreciated that the axial and rotational movements of the tube through the inspection station are tracked such that the computer can exactly locate the inspection points on the tube where each of the dimensional and flaw probings are effected by transducers X1, X2 and X4-X7 during each inspection cycle. Thus, the tube locations of out-of-tolerance dimensions and flaws are identified for subsequent visual inspection by quality assurance personnel.

It is seen that the objects set forth above, including those made apparent from the foregoing Detailed Description, are efficiently attained, and, since certain changes may be made in the construction set forth without departing from the scope of the invention, it is intended that all matters of detail be taken as illustrative and not in a limiting sense.

Having described the invention, what is claimed as new and desire to secure by Letter Patent is:

1. A system for non-destructive flaw and dimensional inspection of thin-walled tubular elements, said system comprising, in combination:

A. a first plurality of ultrasonic transducers for dimensionally inspecting a tubular element along respective helical scanning paths;

B. a second plurality of ultrasonic transducers for flaw inspecting the tubular element along respective helical scanning paths;

C. a separate driver for respectively electrically exciting each said transducer of said first plurality to emit dimensional probing ultrasonic energy pulses and each said transducer of said second plurality to emit flaw probing ultrasonic energy pulses, all directed at the tubular element through a fluid couplant;

D. a separate RF channel for respectively handling echo signals received by each said transducer of said first and second pluralities;

E. a multiplexor having a separate input connected to each said RF channel and a single output;

F. an amplifier having an input connected to said multiplexor output and an output;

G. a signal splitter having an input connected to said amplifier output and a plurality of outputs;

H. a separate signal detector channel connected to each said splitter output, each said detector channel including a discriminator for generating a time mark signal in response to an echo signal, at least one of said detector channels further including a peak detector for generating a signal indicative of the peak to peak amplitude of an echo signal;

I. separate timing means connected to each said detector channel; and

J. synchronizer means for generating a succession of timing pulses to synchronize
   1) the electrical excitation of said transducers of said first and second pluralities by said drivers,
   2) the operation of said multiplexor in successively connecting each of its said inputs to its said single output, and
   3) said timing means such as to separately indicate the elapsed times between the emissions of said probing ultrasonic energy pulses and the receipts of corresponding ultrasonic energy pulse echoes by each said transducer.

2. The system defined in claim 1, which further includes means controlled by said synchronizer timing pulses for generating inspection windows in said discriminators and said peak detector during which responses to said echo signals are permitted.

3. The system defined in claim 2, which further includes a computer connected to receive said peak amplitude indicating signals from said peak detector.

4. The system defined in claim 3, wherein said timing means are embodied in a time-to-digital converter connected to enter said separate elapsed time indications into said computer.

5. The system defined in claim 4, wherein any said echo signals produced by said transducers of said second plurality are successively detected by a single said peak detector in one said detector channel.

6. The system defined in claim 4, wherein said first plurality of transducers includes first and second transducers respectively situated a known distance apart in diametrically opposed relation to the tubular element, said first and second transducers respectively producing a succession of first, second and third echo signals in response to ultrasonic energy pulses reflected from the outer surface, the inner surface and again from the inner surface, respectively, of the tubular element, said first, second and third echo signals of said first transducer being detected by the one of said discriminators in a first one of said detector channels pursuant to generating respectively corresponding first, second, and third time mark signals, said first, second, and third echo signals of said second transducer being detected by the one of said discriminators in a second one of said detector channels pursuant to generating respectively corresponding fourth, fifth and sixth time mark signals, said timing means including a plurality of clocks commonly started at the beginning of an inspection cycle and separately stopped by said time mark signals, whereby to provide elapsed time data from which said computer can calculate dimensional data for the tubular element.

7. The system defined in claim 6, wherein said second plurality of transducers are situated relative to the tubular element to internally probe the wall thereof with ultrasonic energy pulses propagating in opposite longitudinal and circumferential directions, an echo signal produced by any transducer of said second plurality in response to ultrasonic energy pulses reflected from a flaw being detected by said peak detector for generating said peak to peak amplitude indicative signals and by the one of said discriminators in a third one of said detector channels for generating a seventh time mark signal, a separate clock in said timing means being stopped by said seventh time mark signal whereby to provide elapsed time date from which said computer can determine flaw location.

8. The system defined in claim 7, which further includes a compensating transducer for producing a reference echo signal, one of said discriminators in a fourth one of said detector channels generating an eighth time mark signal in response to said reference echo signal for stopping a separate clock in said timing means to provide elapsed time data indicative of ultrasonic energy propagation velocity in the fluid couplant, thereby enabling said computer to calculate a correction factor compensating for variations in couplant temperature.

9. The system defined in claim 7, wherein said discriminators are constant fraction discriminators.

10. The system defined in claim 9, which further includes an additional signal detector channel for conducting echo signals to a cathode ray tube display.

* * * * *